United States Patent [19]
Maas

[11] 3,958,134
[45] May 18, 1976

[54] INSTALLATION FOR THE DETECTION AND PROCESSING OF ELECTRICAL SIGNALS

[75] Inventor: Michael Maas, Erlangen, Germany

[73] Assignee: Siemens Aktiengesellschaft, Erlangen, Germany

[22] Filed: Dec. 16, 1974

[21] Appl. No.: 533,444

[30] Foreign Application Priority Data
Dec. 19, 1973  Germany.......................... 2363218

[52] U.S. Cl............................ 307/235 K; 328/115
[51] Int. Cl.$^2$ ......................................... H03K 5/20
[58] Field of Search ........................ 328/115–117; 307/235 R, 235 K

[56] References Cited
UNITED STATES PATENTS
3,737,790  6/1973  Brown........................... 328/115 X

*Primary Examiner*—John Zazworsky
*Attorney, Agent, or Firm*—Haseltine, Lake & Waters

[57] ABSTRACT

An installation for the detection of and, respectively, processing of electrical signals, particularly physiological measuring signals, for example EKG, through the intermediary of a signal rectifier, and a thereto connected threshold discriminator having a threshold adjusted to a predetermined amplitude value of the rectified signals. The installation includes a signal polarity detector which is actuated by the threshold discriminator and, at the instant of exceeding or transgressing of the threshold of the threshold discriminator, detects the polarity of the threshold exceeding signal amplitude preceding the rectifier, and which superimposes upon the signals preceding the rectifier a direct potential having a polarity in conformance with the detected signal polarity until at least the occurrence of the subsequent exceeding of the threshold, and wherein the direct potential indicates an amount lying between zero and the threshold level of the threshold discriminator.

6 Claims, 3 Drawing Figures

INSTALLATION FOR THE DETECTION AND PROCESSING OF ELECTRICAL SIGNALS

FIELD OF THE INVENTION

The present invention relates to an installation for the detection of and, respectively, processing of electrical signals, particularly physiological measuring signals, for example EKG, through the intermediary of a signal rectifier, and a thereto connected threshold discriminator having a threshold adjusted to a predetermined amplitude value of the rectified signals.

DISCUSSION OF THE PRIOR ART

Installations of this type are employed in particular in the EKG measuring technology for the detection of the R-waves or displays of the EKG, and operate error-free only when, in actuality, only genuine R-displays or waves alone exceed the threshold of the threshold discriminator. However, it frequently occurs that the EKG signal evinces further signal components in addition to the R-displays, which may be so high in their amplitude so as to also similarly lie above the threshold of the threshold discriminator. Such signal components, for example, are excessively high (polarized in reverse to the R-displays) Q-or S peaks, or the like static or interference voltages which have been thrown in through the EKG output electrodes or, for example, also through the signal preprocessing elements, for example, amplifiers, or the like. It has been previously attempted to extensively suppress the signal components which impart an interfering effect to the signal processing by incorporating an electronic gate in the signal channel, which is always opened only for a short time only after a predetermined delay interval after the occurrence of a threshold transgression for allowing the through-passage of further signal components (for the expected subsequent R-wave or display). The suppression of static or interference by means of electronic gates does not, however, provide optimum results inasmuch as the open time period of the gate with regard to the expected oscillation span of the time interval between the occurrence of two R-displays in the EKG is not sufficiently small, in effect, detrimentally to the particular blanking or black-out time interval of the electronic gate cannot be selected so as to be sufficiently large. Due to the hereby required relatively large opening-blanking or blacking-out time ratios for the gate, it thus may occur that static or interference impulses coincide with the opening interval of the gate, and may in an undesirable manner thereby still gain entry for further processing.

SUMMARY OF THE INVENTION

Accordingly, it is an object of the present invention to provide an installation of the above-mentioned type in which the elimination of the static or interference signal components is carried out at a much greater factor of assurance than in connection with the usual known installations.

The foregoing object is inventively solved by means of a signal polarity detector which is actuated by the threshold discriminator and, at the instant of exceeding or transgressing of the threshold of the threshold discriminator, detects the polarity of the threshold exceeding signal amplitude preceding the rectifier, and which superimposes upon the signals preceding the rectifier a direct potential having a polarity in conformance with the detected signal polarity until at least the occurrence of the subsequent exceeding of the threshold, and wherein the direct potential indicates an amount lying between zero and the threshold level of the threshold discriminator.

In the carrying out of the object of the invention it is assumed that for electrical signals having such positive and negative signal components which, after rectification thereof, both equally lead to exceeding or transgressing of the threshold, those signal components which are of actual interest for the further utilization thereof (for example, the R-displays in the EKG) are, in the normal instance, always received at the same polarity (in effect, either only positive or only negative), and in particular with merely randomly encountered oppositely polarized interference signal peaks, also occur at a greater frequency then the latter. Due to this actual relationship, in the inventive installation, in the normal instance after the initial occurrence of a threshold-exceeding interesting signal component (for example, the initial receipt of an R-wave or display in the EKG), the electrical signal has subsequently practically continuously superimposed or impressed thereon from occurrence to incurrence of further such signal components, a direct potential having the polarity of these interesting signal components. Hereby, (at a suitable selection of the direct potential value) there are also displaced in the polarization direction of the direct potential eventual high-amplitude, oppositely polarized signal components (for example, the Q-or S-components which are polarized oppositely to the R-display, and respectively also the randomly thrown-in oppositely polarized static or interference wave peaks) to such an extent as to be located below the threshold of the threshold discriminator after rectification. The installation according to the invention thus automatically searches out, on the one hand, those signal components from a measuring signal mixture having relatively high positive and negative signal components, which occur particularly frequently with a predetermined polarity, and preferentially raises these signal components above the threshold of the threshold discriminator, whereas oppositely polarized signal components are practically always initially damped or attenuated below the threshold of the threshold discriminator.

Thereby, the inventive installation, in contrast with the usual installations with, for example, electronic gates, has the significant additional advantage that at least the signal components which are oppositely polarized with respect to the signal components which are of interest, and as experience has shown carry intensive interferences therewith, are already suppressed below the threshold value of the threshold discriminator even before reaching the latter. Measuring errors which may occur, for example, in gate suppression circuitry through respective static stray effects during the gate opening time interval, are hereby avoided from the very beginning. On occasion strayed in static or interference signals with the same polarity as the interesting signal components exceeding the threshold may thus be only conditionally blocked-out by means of the inventive installation (for example, in combination with electronic blocking gates). Due to the inventively total suppression of the primary interfering oppositely poled signal components, such static or interference signals are, however, in the event that they actually occur, extremely infrequent and thus also quite readily recognizable as static or interference stray effects (in any case, with much greater assurance than previously).

BRIEF DESCRIPTION OF THE DRAWING

Further advantages and details of the invention may now be ascertained from the following description of an exemplary embodiment thereof with regard to EKG processing, taken in conjunction with the accompanying drawings; in which.

DETAILED DESCRIPTION

Figure 1:
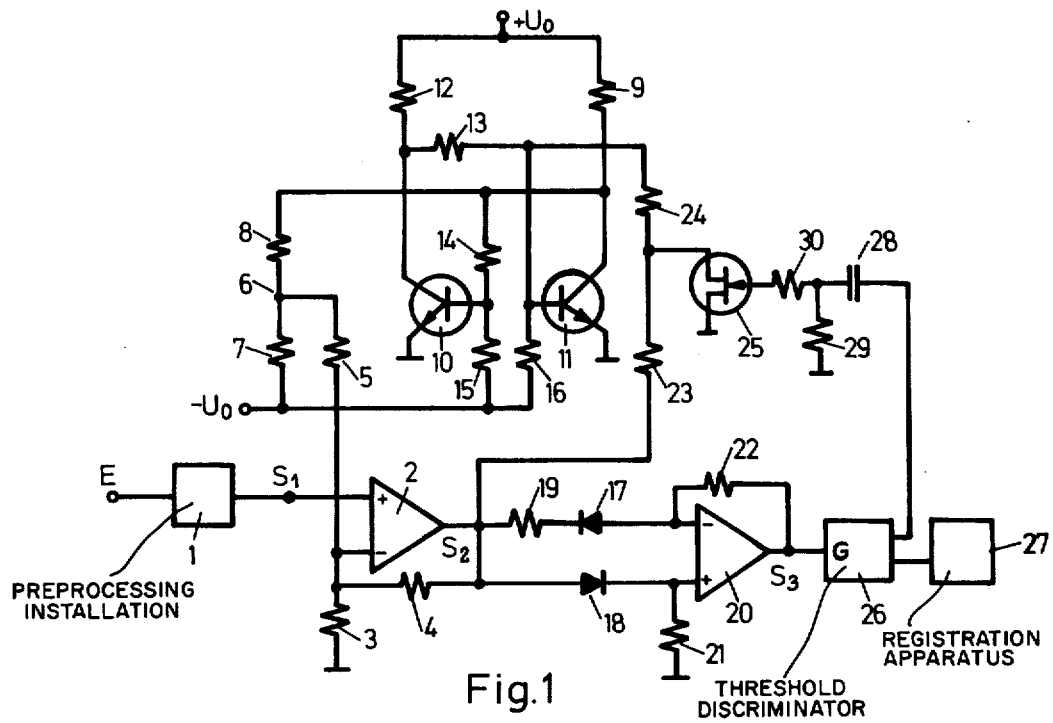
FIG. 1 diagrammatically illustrates the primary schematic circuit of the inventive installation.

In the basic schematic circuit shown in FIG. 1 of the drawing, the EKG signals which are taken of, for example, by electrodes on the body of a patient, are conducted to the input E of a preprocessing installation 1 (containing, for example, a preamplifier for the EKG signals, a band-pass for, for example, the selection of the frequencies which are significant for the QRS-complex, and also, as occasioned, an amplitude compensating regulating circuit for the R-wave or display amplitudes). The signals $S_1$ received at the output of the preprocessing installation are then transmitted to the non-inverted input of an operational amplifier. The inverted input of the operational amplifier is herewith connected, on the one hand, through an ohmic resistance 3 with ground and, on the other hand, coupled through an ohmic resistance 4 with the amplifier output. The inverted input of the amplifier 2, furthermore, is also connected through an ohmic resistance 5 with the divider tapoff 6 of an asymmetrical voltage divider which is constituted of ohmic resistances 7, 8, 9 (resistances 8 and 9 are lower than resistance 7). This voltage divider or direct potential generator superimposes a direct potential on the EKG signal at the output of the operational amplifier 2 whose polarity may be either positive or negative, in accordance with the switching condition of a bistable flip-flop connected preceding the voltage divider, and which consists of two transistors 11 and 10, as well as ohmic switching resistances 9, 12 through 16, as subsequently more detailed described.

The output signal $S_2$ of the operational amplifier 2 is, on the one hand, transmitted to a full-wave rectifier which is constructed of diodes 17 and 18, a series resistance 19, as well as an amplifier 20 having switching resistances 20 and 22, and, on the other hand, across the resistances 23 and 24 with a therebetween switched field-effect transistor 25, to the control input of the bistable flip-flop 9 through 16 (base of the transistor 11). The field-effect transistor 25 is hereby found in a conductive condition as long as the output signal $S_3$ at the output of the full-wave rectifier 17 through 22 does not exceed or cross over the threshold G of a threshold discriminator 26 as shown, for example, in U.S. Pat. No. 3,554,188, which is adjusted to a voltage value proximate the R-display or wave peaks of the EKG signals (for example, monostable flip-flop or stepping oscillator with threshold transistor). The field-effect transistor thereby short-circuits across its source drop-off section, for these time spans, the not yet rectified EKG signals passing across the resistance 23. If, in contrast therewith, the EKG signals exceed in amplitude the set threshold value G of the threshold discriminator 26, then the latter at a first ouput generates a first indicating impulse for the carried out threshold exceeding or crossing, which is transmitted to a registration or, eventually, processing apparatus 27 (for example, a counter circuit or the like) for indicating or, respectively, for further processing.

The threshold discriminator 26, in addition to this first indicating impulse, further generates at each threshold value trespassing at a further output additionally also, for a short term, a second negative indicating impulse which is directly transmitted through an RC-element 28, 29, as well as an ohmic resistance 30, to the control electrode of the field-effect transistor 25. The field-effect transistor 25 is controlled into a blocked condition for a short time by means of this negative impulse, so that now, for a similar short time, the threshold exceeding amplitude preceding the full-wave rectifier 17 through 22, is applied through resistances 23 and 24 to the base of the transistor 11 of the bistable flip-flop 9 through 16. If thereby the threshold exceeding signal amplitude is, for example, initially positive, then the bistable flip-flop 9 through 16 is, for instance, tilted into a first stable condition in which the transistor 11 is conductive and, in contrast therewith, the transistor 10 is blocked. Through the conductive transistor 11, the resistance 8 of the voltage divider 7 through 9 has ground potential applied thereto, and thereby the potential of the divider tapoff 6 is displaced towards a negative value. This negative potential value is herewith selected to be so large that, after inversion through the operational amplifier 2, that the positive direct potential superimposed or impressed on the output signal $S_2$ of the amplifier is approximately 20 percent of the threshold value of the threshold discriminator 26. If, in contrast therewith, the threshold exceeding amplitude is negative, then the bistable flip-flop 9 through 16 is tilted into its second stable condition. In the now blocked transistor 11 there is formed a positive direct potential at the divider tapoff 6 of the voltage divider 7 through 9 due to the positive operating voltage $+U_0$ of the bistable flip-flop applied to the resistances 9 and 8. After inversion through the amplifier 2, there is thus superimposed a negative potential on the EKG signal $S_2$, wherein this value lies again at approximately 20 percent of the threshold value of the threshold discriminator 26.

Figure 2:
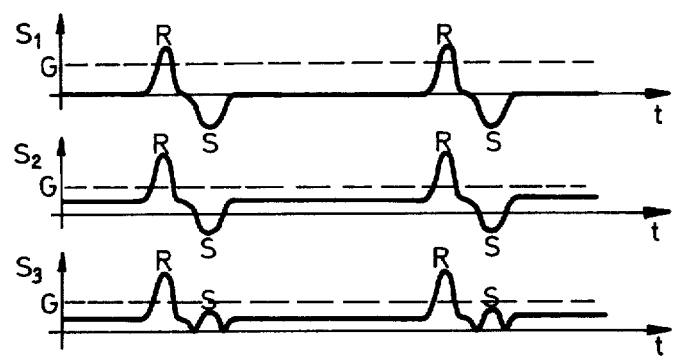
FIG. 2 shows an EKG-signal schematic which illustrates diagramatically the suppression sequence of negative EKG signal components at a positive R-display for the EKG signal.
Figure 3:
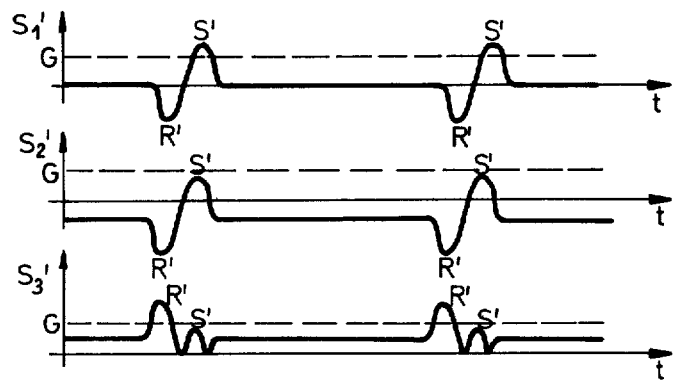
FIG. 3 is a corresponding signal schematic for negative R-displays in the EKG.

The influence of the particular positive or negative direct potential impressed on the EKG signal is, for example, illustrated in FIGS. 2 and 3.

FIG. 2 of the drawing shows, as $S_1(t)$, the time sequence of an EKG which prefers positive R-displays or waves and, for instance, corresponding high-amplitude and detrimentally interfering negative S-waves or displays. By means of $S_2(t)$, there is indicated in contrast therewith, due to the preferred positive R-displays, practically continually the output EKG of the operational amplifier 2 having the positive direct potential superimposed thereon. From $S_3(t)$, meaning the signal sequence of the rectified EKG signals having the positive direct potential superimposed thereon, there may finally be ascertained that the negative S-peaks are now more clearly suppressed below the threshold G of the threshold discriminator 26, and thereby can no longer lead to transgression errors. FIG. 3, in contrast therewith, merely shows the reversed case, meaning the signal sequences $S_1'(t)$, $S_2'(t)$, $s_3'(t)$ for EKG signals with, preferably, negative R-displays or waves and, accordingly, positive S-waves and with a superimposed negative direct potential.

The S-wave suppression described on the basis of FIGS. 2 and 3 is, naturally, only of an exemplary character. In addition to the S-wave, by means of the inventive installation according to FIG. 1, there are naturally automatically suppressed in the same manner also any other high-amplitude static or interference components which are oppositely polarized with respect to the R-displays or waves (for example, also thrown-in static components). The inventive interference suppression is herewith carried out also completely independently of an eventual additionally provided electronic gate of the above-described type (for example, in the construction of the threshold discriminator 26 as a monostable flip-flop, whose return oscillating time point after the particular carried-out threshold exceeding may be correspondingly more or less delayed). That type of additional gate namely is suitable, but is not absolutely essential.

While there has been shown what is considered to be the preferred embodiment of the invention, it will be obvious that modifications may be made which come within the scope of the disclosure of the specification.

What is claimed is:

1. In an installation for the detection and, respectively, processing of electrical signals, in particular physiological measuring signals, such as EKG, including said signal signal channel, a signal rectifier for said signals in said channel; and a threshold discriminator at the output of said rectifier having a threshold set to a predetermined amplitude value of the rectified signals, the improvement comprising: a signal polarity detector actuated by said threshold discriminator for detecting the polarity of the threshold-exceeding signal amplitude preceding the rectifier at the instance of exceeding the threshold value of said threshold discriminator; and a direct potential generator actuated by said signal polarity detector for superimposing on the signals preceding said rectifier a direct potential of a polarity in conformance with the polarity of the detected signal at least until the incidence of a successive exceeding of said threshold value, whereby said direct potential has a value ranging between zero and the threshold value of said threshold discriminator.

2. Installation as claimed in claim 1, said signal polarity detector consisting of a bistable flip-flop, said flip-flop adapted to be switched into one or the other of the stable conditions thereof dependent upon positive or negative thresholdexceeding signal components.

3. Installation as claimed in claim 1, comprising switch means for coupling said signal polarity detector in the signal channel preceding said rectifier, said switch means adapted to be actuated responsive to a voltage impulse indicative of exceeding a threshold value of said threshold discriminator.

4. Installation as claimed in claim 3, said switch means comprising a field-effect transistor for short-circuiting the electrical signal connection between the signal channel and said signal polarity detector arrangement responsive to the absence of an output signal from said threshold discriminator, and adapted to be controlled into a blocking condition for a short time interval for intermittent lifting of said electrical signal connecting interruption responsive to exceeding of the threshold value of said threshold discriminator.

5. Installation as claimed in claim 2, said direct potential generator comprising an asymmetrical voltage divider having a dividing end point constantly located at one of the two mutually opposed operating voltages of said flip-flop and wherein, upon actuation of the other of the two flip-flop operating voltages, in the one stable oscillated condition or the zero potential in the other stable oscillated condition at the second dividing end point of the divider potential, the divider tapoff coupled to the signal channel preceding said rectifier is displaced towards a respectively positive or negative direct potential.

6. Installation as claimed in claim 1, said positive or negative direct potential superimposed on said electrical signal preceding said rectifier being approximately 20 percent of the threshold value of said threshold discriminator.

* * * * *